United States Patent [19]

Flentge et al.

[11] Patent Number: 4,543,412

[45] Date of Patent: Sep. 24, 1985

[54] PHENOBARBITAL ENZYME INHIBITORS

[75] Inventors: Charles A. Flentge, Lake Villa; Thomas R. Herrin, Waukegan, both of Ill.

[73] Assignee: Abbott Laboratories, North Chicago, Ill.

[21] Appl. No.: 548,743

[22] Filed: Nov. 4, 1983

[51] Int. Cl.[4] .................. A61K 31/675; A61K 31/69; C07F 5/02; C07F 9/65
[52] U.S. Cl. ..................................... 544/229; 544/243
[58] Field of Search ................................ 544/243, 229

[56] References Cited

U.S. PATENT DOCUMENTS 4,273,866 6/1981 Voss et al. ...................... 544/244 X
4,451,652 5/1984 Flentge et al. ...................... 544/229

Primary Examiner—Donald G. Daus
Assistant Examiner—Diana G. Rivers
Attorney, Agent, or Firm—Martin L. Katz; Margaret M. O'Brien; James L. Wilcox

[57] ABSTRACT

Phenobarbital conjugates for use as enzyme inhibitors having the formula:

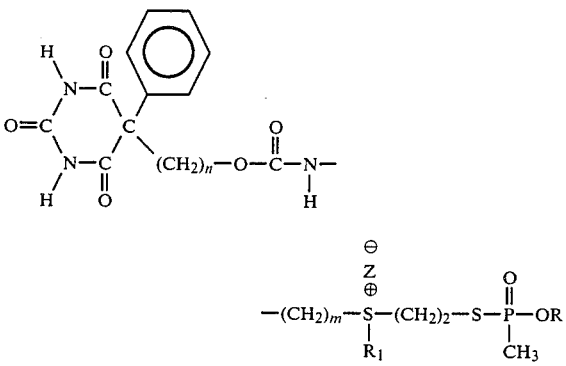

wherein Z is a biologically compatible counter ion, n and m is an integer from 2 to 6 and R and $R_1$ are each lower alkyl.

7 Claims, No Drawings

PHENOBARBITAL ENZYME INHIBITORS

This invention relates to phenobarbital conjugates, and more particularly to phenobarbital-thiophosphonate conjugates for use as enzyme tracers.

There is described in U.S. Pat. No. 4,273,866 a technique for determining the presence of ligands in test samples in which a test sample is mixed with a ligand analog-irreversible enzyme inhibitor conjugate as well as a binding protein bindable to the ligand and the ligand analog-irreversible inhibitor conjugate. As described in that patent, the amount of ligand analog-irreversible enzyme inhibitor conjugate bound by the binding protein is related to the amount of ligand test sample. Thus, the techniques as described in that patent provide a convenient immunoassay technique for measuring the amount of a variety of drugs, hormones and like biological fluids.

The present invention relates to novel conjugates of phenobarbital which can be used in the immunoassay technique described in the foregoing patent.

The concepts of the present invention reside in compounds having the formula:

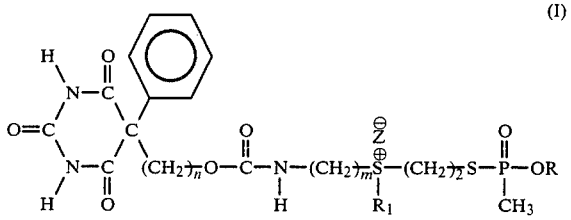

(I)

wherein Z is a biologically compatible counter ion, n and m are each independently an integer from 2 to 6 and R and $R_1$ are each independently a lower alkyl group, and preferably one containing 1 to 5 carbon atoms (e.g., methyl, ethyl, propyl, n-butyl, tert-butyl, etc.).

As used herein, the term "biologically compatible counter ion" refers to anions represented by "Z" including, for example, chloro, iodo, methylsulfate, tetrafluoroborate and the like.

The compounds of the present invention are useful as tracers for acetylcholinesterase in immunoassays for the determination of phenobarbital in serum or plasma. Such compounds can be used, for example, in the immunoassay technique described in U.S. Pat. No. 4,273,866, the disclosure of which is incorporated herein by reference.

The compounds of the present invention are prepared using standard synthetic techniques. A 5-hydroxy phenobarbital analog is first reacted with phosgene to form the corresponding acetyl chloride derivative as illustrated by the following:

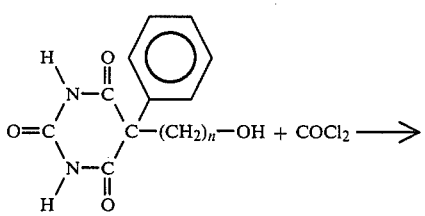

(II)

-continued

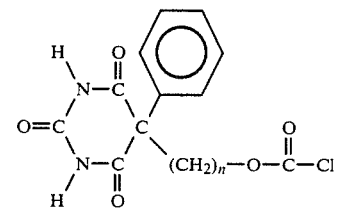

In a separate step, an n-butoxycarbonyl protected phosphonate is, in accordance with the teachings of U.S. Pat. No. 4,273,866, converted to the corresponding trifluoroacetic salt as illustrated below:

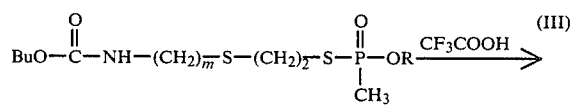

(III)

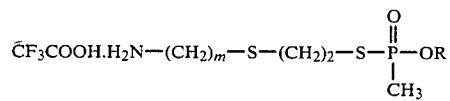

The amide derivative of phenobarbital is then prepared by reacting the trifluoroacetic salt of the phosphonate with the acetylchloro derivative of phenobarbital to produce the following compound:

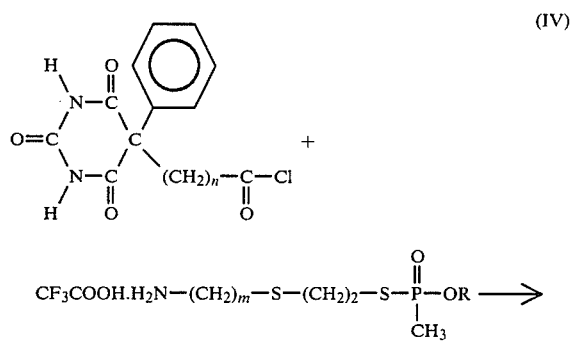

(IV)

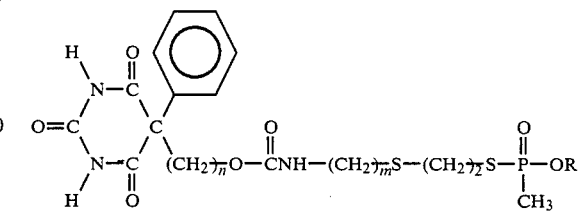

Finally, in the last step, compound IV is reacted with an alkyl iodide and preferably methyl iodide in the presence of a Lewis acid catalyst such as silver tetrafluoroborate to produce the compounds of the invention.

As indicated above, the compounds of the present invention can be used in the immunoassay for phenobarbital in accordance with the techniques described in U.S. Pat. No. 4,273,866. Generally, in the use of the compounds of the invention, the phenobarbital in a serum specimen is mixed with a specific antibody against phenobarbital, the enzyme acetylcholinesterase, the phenobarbital analogs of the present invention, the enzyme substrate which is typically acetyl-beta-(methylthio)choline iodide and a reagent to produce the chromogenic product, usually 5,5'-dithiobis-(2-nitrobenzoic) acid. As those skilled in the art appreciate, the phenobarbital present in the specimen and the phenobarbital analog compete for a limited number of binder sites on the antibody, the degree of binding of each being proportional to their respective concentrations. The phenobarbital analogs of the present invention, which are unbound rapidly and irreversibly, inhibit the enzyme while the analog bound by the antibody has no inhibitory effect on the enzyme. Thus, the amount of enzyme activity which is inhibited is related to the concentration of the phenobarbital in the specimen.

As is described in the foregoing patent, such enzyme activity can be measured colorimetrically. The active enzyme activates the substrate which further reacts to produce a chromogenic product. Spectrophotometric absorbence readings can thus be made, the intensity of the phenobarbital being present in the specimen.

The immunoassay can be performed at ambient temperatures although, as will be appreciated by those skilled in the art, temperatures ranging from ambient to physiological temperatures can be used with facility. Reaction times are dependent on temperature and reagent dilution.

Having described the basic concepts of the present invention, reference is now made to the following example which is provided by way of illustration of the practice of the invention of the preparation of the phenobarbital conjugates.

EXAMPLE 5-hydroxyethyl-5-phenobarbituric acid (4.0 g) is added to freshly distilled tetrahydrofuran. Phosgene gas is passed through the solution for 10 minutes until all the material has solubilized. Nitrogen gas is passed through the solution for one hour and solvent is removed by evacuation. The residue is dried under vacuum to give 4.6 g (92%) as a white solid (II).

The butoxycarbonyl thiophosphonate (V, 1.4 g)

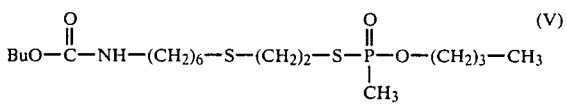

is taken up in methylene chloride (4 ml) and cooled to 0° C. Trifluoroacetic acid (4 ml) is added and the reaction is stirred for 30 minutes at 0° C. Solvent is removed to give a quantitative yield (1.4 g) of (VI) as an oil.

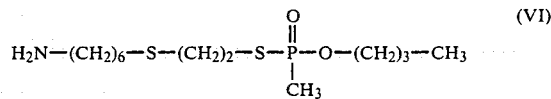

Compound (VII, 2.1 g) is taken up in methylene chloride and triethylamine is added to pH 9. The chloroformate (II, 1.5 g) is added and the reaction is stirred for 2 hours. The reaction mixture is washed with brine, water and dried over magnesium sulfate. Solvent is removed to yield 1.3 g of (VII) as an oil.

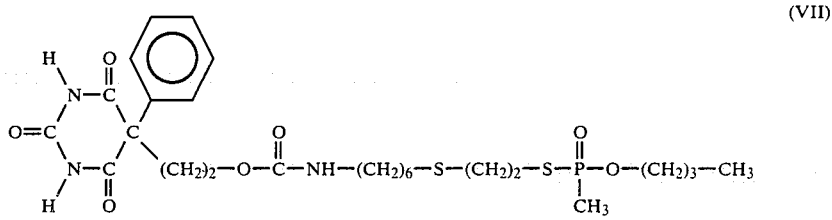

Compound (VII, 1.1 g) is taken up in methylene chloride (4 ml) and methyl iodide (4 ml) is added. Silver tetrafluoroborate (0.5 g) is added and the reaction is stirred at room temperature for 30–45 minutes. Silver iodide is removed by filtration and solvent removed to give crude (VIII). Purification is performed on a Waters Prep 500A unit eluting with 75/25/.01M methanol-water-trifluoroacetic acid to give 0.61 g of (VIII).

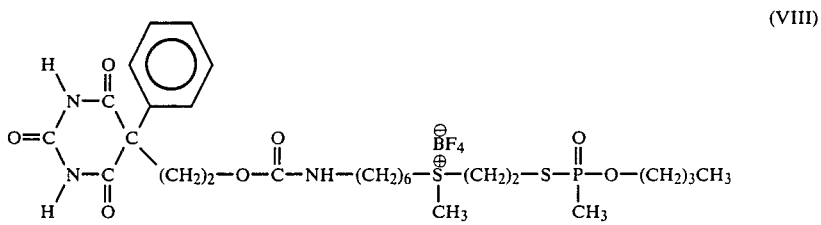

The compound was determined to have a second order rate constant for the inhibition of acetylcholinesterase of $3.5 \times 10^8$ liter mole$^{-1}$ min$^{-1}$.

As will be understood by those skilled in the art, the biologically compatible counter ion is derived from the Lewis acid employed in the last step of the reaction. Other Lewis acids well known to those skilled in the art may be used in lieu of silver tetrafluoroborate, including metal salts containing, as the anion, chloro, iodo and methyl sulfate groups to produce compounds having the corresponding biologically compatible counter ion.

It will be understood that various changes and modifications can be made in the details of procedure, formulation and use without departing from the spirit of the invention, especially as defined in the following claims.

What is claimed is:

1. A compound having the formula:

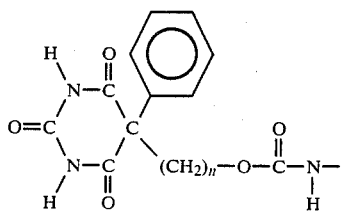

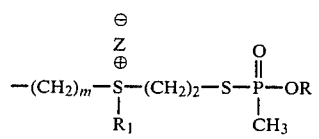

wherein Z is a biologically compatible counter ion, n and m are each independently an integer from 2 to 6 and R and $R_1$ are each independently lower alkyl.

2. A compound as defined in claim 1 wherein n is 2 and m is 6.

3. A compound as defined in claim 1 wherein R is a butyl group.

4. A compound as defined in claim 1 wherein $R_1$ is methyl.

5. A compound as defined in claim 1 wherein n is 2, m is 6, R is butyl and $R_1$ is methyl.

6. A compound as defined in claim 1 wherein Z is selected from the group consisting of chloro, iodo, methyl sulfate and tetrafluoroborate ions.

7. A compound as defined in claim 5 wherein Z is the tetrafluoroborate ion.

* * * * *